United States Patent [19]

Turley

[11] Patent Number: 5,279,554
[45] Date of Patent: Jan. 18, 1994

[54] IMPLANTING DEVICE

[75] Inventor: Roger W. Turley, Haverhill, Great Britain

[73] Assignee: Rhone Merieux, Lyons, France

[21] Appl. No.: 915,728

[22] Filed: Jul. 29, 1992

[30] Foreign Application Priority Data

Feb. 9, 1990 [GB] United Kingdom ................ 9002967

[51] Int. Cl.⁵ ............................................. A61M 31/00
[52] U.S. Cl. ............................................................ 604/60
[58] Field of Search ...................... 604/59, 60, 61, 158, 604/164, 57; 606/116, 117; 600/7, 8

[56] References Cited

U.S. PATENT DOCUMENTS

| 4,661,103 | 4/1987 | Harman | 604/62 |
| 4,787,384 | 11/1988 | Campbell | 606/117 |
| 4,820,267 | 4/1989 | Harman | 604/60 |
| 4,846,793 | 7/1989 | Leonard et al. | 604/62 |
| 4,915,686 | 4/1990 | Frederick | 604/60 |
| 4,994,028 | 2/1991 | Leonard et al. | 604/60 |

FOREIGN PATENT DOCUMENTS

| 0304107 | 2/1989 | European Pat. Off. |
| WO304 | 2/1984 | PCT Int'l Appl. |
| WO6905 | 9/1988 | PCT Int'l Appl. |

*Primary Examiner*—Jerome L. Kruter
*Attorney, Agent, or Firm*—Larson and Taylor

[57] ABSTRACT

A device for implanting an object, such as a hormone pellet or an electronic transponder beneath the skin of an animal, includes a hollow needle (1) with an actuating rod (11) slidable therein, a cover (2) movable relative to the needle to enable at least the sharp end of the needle to be shrouded, and a locking mechanism in the form of an abutment (10) movable into a rebate (6), from which it cannot then return. The needle (11) may be mounted at one end of a body (4) which incorporates the locking rebate (6).

6 Claims, 1 Drawing Sheet

IMPLANTING DEVICE

FIELD OF THE INVENTION

The invention relates to a device for implanting an object beneath a membrane such as the skin of an animal. Although described in relation to the implanting of electronic tracer devices in animals the invention is applicable to the implanting of other objects for example hormone pellets, beneath the skin of animals, or small objects into reaction vessels covered by a stretched membrane.

BACKGROUND TO THE INVENTION

It is known to implant pellets, such as hormone pellets, beneath the skin of an animal using a device having a hollow needle through which a rod may travel to transfer the pellets from the needle to the animal. An example of such a device is described and illustrated in the specification of our published UK Patent Application No. GB2190590A.

One disadvantage associated with this sort of device is that the device may inadvertently be used more than once on a number of animals, giving rise to the risk of cross infection. In addition, a used needle presents the danger of injury and infection to someone handling the device.

SUMMARY OF THE INVENTION

According to the invention there is provided a device for implanting or injecting an object beneath a membrane, the device comprising: a needle from which, in use, the object is transferred to a position beneath the membrane; a cover which is movable between a retracted position in which the needle can penetrate the membrane, and an extended position in which the needle is at least partially shrouded; and a locking mechanism for locking the cover in the extended position, to prevent the device from being used for more than one operation and shroud at least the sharp end of the needle.

Thus, after the device has been used, the cover is locked into a position which is such that the needle is unlikely to cause injury or contamination or infection (depending what it has been used for).

The locking mechanism may be operated by means of a lever or switch provided on the device. Preferably however it is operated automatically by moving the cover into the extended position, and where the locking mechanism operates in this way, operation of the device preferably involves moving the cover from the retracted position, to the extended position, so as to prevent the cover from being left inadvertently in the retracted position after use.

When in the extended position, it may be sufficient for the cover to shroud only the sharp end region of the needle. However, the cover preferably comprises a sleeve which is slidably mounted relative to the needle and which, when extended, shrouds the whole of the needle.

The device may be of the kind in which the needle is hollow, and which includes expulsion means comprising a rod which is a sliding fit within the needle, and which travels along the needle to transfer an object located in the hollow interior of the needle to below the membrane. In this case, the needle is preferably mounted at one end of a body relative to which the cover is slidably mounted and the rod is mounted on the cover.

The locking mechanism for this device may comprise a resiliently deformable protruberance, projecting from either the cover or the body, and a corresponding recess in the other of the two parts, the arrangement being such that the protruberance, in use, engages the recess to lock the cover in the extended position.

The device may include a handle which may with advantage be demountable and which may be packed as a separate component and may be mounted on the device by for example a friction fit or by interengagement of mounting formations on the handle and on the device.

The invention is of particular application to an implanting device for penetrating the skin of an animal and depositing therebelow an object such as the electronic transponder identity tag; or hormone pellets and the like.

The invention also lies a method of implanting a device below a membrane using the apparatus on aforesaid so that the penetrating needle is shrouded after use.

BRIEF DESCRIPTION OF THE DRAWINGS

The invention will now be described, by way of example only, with reference to the accompanying drawings in which.

DETAILED DESCRIPTION

The device shown in the Figures is used to implant a tracer device comprising a solid state transponder beneath the skin of live stock. The transponder is the kind which, in use, emits an electro-magnetic location signal in response to receiving an interrogating signal from a remote transmitter.

Figure 1:
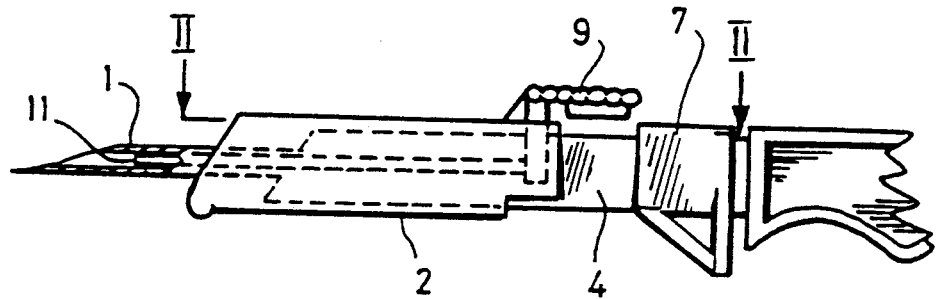
FIG. 1 is a side view of a device according to the invention.
Figure 2:
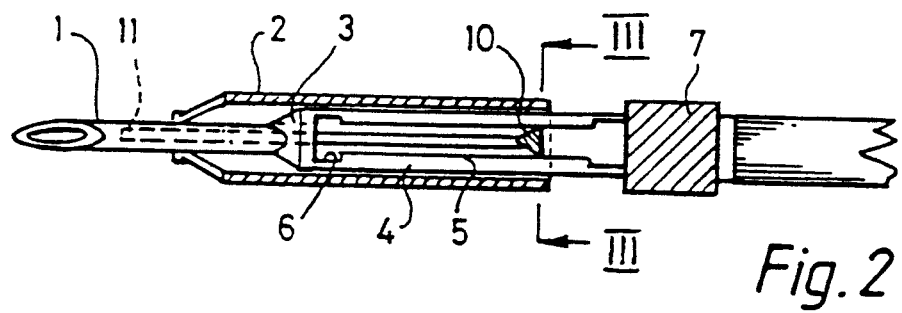
FIG. 2 is a section taken along the line II—II of FIG. 1.
Figure 3:
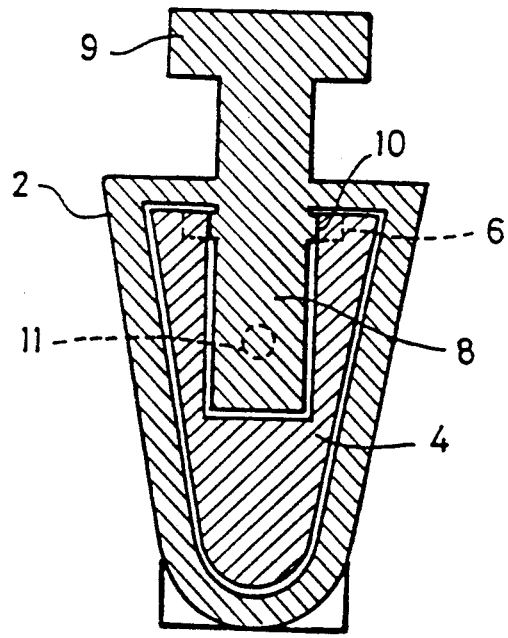
FIG. 3 is a section taken along the line III—III of FIG. 2.

Referring to FIG. 1, the device comprises a hollow needle 1 and a cover 2 which is movable relative to the needle 1. The cover 2 is shown in a retracted position in FIGS. 1 and 2.

The needle 1 is mounted at one end to an end face 3 (FIG. 2) of an elongate body 4 which is of a generally truncated triangular cross-section.

The body 4 includes a slot or track 5 which runs parallel to the elongate axis of the body 4, and which includes a recess or rebate 6 at one end. An end stop and connector 7 is disposed on the end of the body 4 opposite the end face 3, and includes a triangular section socket (not shown) which faces away from the body 4.

The cover 2 is in the form of a sleeve which has a corresponding section to that of the body 4, and which is slidably mounted on the body 4. The cover 2 includes a slide or spigot 8 which is formed integrally with the cover 2, and includes a head 9. The spigot 8 projects into the body 4 through the slot 5, and also includes a resiliently deformable abutment 10 situated within the track 5. When not deformed, the abutment 10 has a width dimension greater than that of the track 5, but less than that of the rebate 6. Thus the abutment is compressed when situated in the slot 5, and will have a width greater than that of the slot 5 when situated in the rebate 6. The abutment 10 is so sized and shaped that it may be moved along the slot 5 into rebate 6, but cannot then return along the slot 5.

A rod 11 is attached to the end of the spigot 8 opposite the head 9, and projects along the body 4 and into the needle 1.

Figure 4:
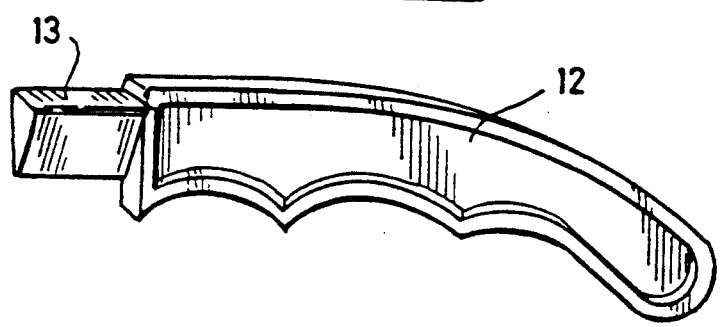
FIG. 4 shows a handle for the device.

Referring to FIG. 4, the device may be attached to a handle 12 having a triangular section plug 13 at one end, which plug 13 is of a corresponding size and shape to the socket in the end connector. The handle 12 may be attached to the device by inserting the plug 13 into the socket in the end connector 7.

The cover 2 may be moved from the retracted position to an extended position in which the rod 11 extends beyond the end of the needle 1, and the abutment 10 is situated in the rebate 6 and the needle 1 situated within the cover 2.

When the device is to be used to implant a tracer, such as a solid state transducer, beneath the skin of an animal, the transducer is placed in the bore of the needle 1, whilst the cover 2 is in the retracted position. The needle 1 is then inserted into the animal and the cover 2 moved towards the extended position. This movement causes the rod 11 to travel along the needle 1, and thus to act as explusion means for transferring the transponder from the needle 1 to the animal. It will be seen that, when the cover 2 abuts the skin of the animal, further movement of the cover relative to body 4 will cause the needle 1 to be withdrawn into the cover 2. Since the distance between the end of the rod 11 and the cover 2 is fixed, this further movement does not affect the position of the transponder which is held in place by the end of rod 11.

This movement is continued until the abutment 10 reaches the rebate 6 at which stage the cover is in the extended position, the needle 1 having been withdrawn from the animal and into the cover 2.

With the cover 2 so positioned, the interaction between the abutment 10 and rebate 6 prevents the cover 2 from being retracted, and thus prevents the device from being used a second time. Furthermore, since the needle 1 is withdrawn into the cover 2, the risk of injury or infection of somebody subsequently handling the device is reduced.

As an alternative to the abutment 10 and rebate 6, the device may have a locking mechanism in the form of a resiliently deformable protruberance on the side of the cover 2 which, in use, engages in a corresponding recess in the body 4. It is also in the scope of the invention for the protruberance to be provided on the body 4 and the recess in the cover 2.

Since the handle 12 is detachable from the rest of the device, the device may be stored, and packaged in a relatively compact form, thus reducing the amount of packaging material needed for the device.

I claim:

1. A device for implanting or injecting an object beneath a skin of an animal, the device comprising:

a body;

a needle attached to said body and extending therefrom, said needle including a sharp end distal from said body which in use is inserted beneath the skin and from inside of which said sharp end the object is transferred to a position beneath the skin;

a cover movably mounted on said body which is adapted to abut the skin of the animal in a retracted position after the sharp end of said needle is inserted beneath the skin and which is moveable on said body between the retracted position and an extended position in which the sharp end of the needle is covered by said cover as the needle is withdrawn from the skin;

a rod attached to a part of said cover and projecting into said needle such that when the body is moved, relative to the cover which is held in contact with the skin, the cover is relatively moved between the retracted and extended positions and said rod acts to expel the object from the needle to the animal without affecting the position of the object beneath the skin; and a locking mechanism for permanently locking the cover against movement once said cover reaches the extended position to prevent the device from being used for more than one operation and to shroud at least said sharp end of the needle.

2. A device according to claim 1 in which said body includes an elongated track; in which said cover comprises an elongated sleeve and a spigot attached to said sleeve and projecting into said track; and wherein said rod is attached to said spigot.

3. A device according to claim 2 in which said locking mechanism comprises resiliently deformable abutment members on said spigot; and a rebate in said track into which said abutment members project when the cover reaches its extended position to lock said sleeve relative to said body.

4. A device according to claim 1 in which the locking mechanism includes a locking member which is operated automatically by moving the cover into the extended position, wherein operation of the device involves moving the cover from the retracted position to the extended position so as to always cause said locking member to be operated and thus to prevent the cover from being left inadvertently in the retracted position after use.

5. A device according to claim 1 and further comprising a handle whereby said handle is demountable as a separate component and a mounting formation on said body which interengages with said handle.

6. A device according to claim 1 wherein an end of said cover which abuts the skin in the retracted position is positioned from said sharp end of said needle by a predetermined distance equal to a desired insertion distance of said needle into the skin.

* * * * *